(12) United States Patent
Su et al.

(10) Patent No.: US 11,364,395 B2
(45) Date of Patent: Jun. 21, 2022

(54) BREATHING MASK WITH INCREASED USER COMFORT

(71) Applicant: KONINKLIJKE PHILIPS N.V., Eindhoven (NL)

(72) Inventors: Wei Su, Shanghai (CN); Qiushi Zhang, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 667 days.

(21) Appl. No.: 16/327,357

(22) PCT Filed: Aug. 17, 2017

(86) PCT No.: PCT/EP2017/070851
§ 371 (c)(1),
(2) Date: Feb. 22, 2019

(87) PCT Pub. No.: WO2018/036902
PCT Pub. Date: Mar. 1, 2018

(65) Prior Publication Data
US 2019/0175962 A1    Jun. 13, 2019

(30) Foreign Application Priority Data

Aug. 24, 2016   (WO) ................ PCT/CN2016/096574
Oct. 24, 2016   (EP) ..................................... 16195216

(51) Int. Cl.
*A62B 18/00* (2006.01)
*A62B 18/08* (2006.01)
(Continued)

(52) U.S. Cl.
CPC ......... *A62B 18/006* (2013.01); *A61M 16/026* (2017.08); *A62B 18/025* (2013.01);
(Continued)

(58) Field of Classification Search
CPC ..... A62B 18/006; A62B 18/025; A62B 18/25; A61B 5/087
See application file for complete search history.

(56) References Cited

U.S. PATENT DOCUMENTS 5,458,137 A    10/1995   Axe
2011/0230779 A1*   9/2011   Titchener ............ A61M 16/026
                                                   600/538

(Continued)

FOREIGN PATENT DOCUMENTS

CN    104548401 A    4/2015
EP    334555 A2    9/1989
(Continued)

*Primary Examiner* — Samchuan C Yao
*Assistant Examiner* — Cana A Gallegos (57) ABSTRACT

A breathing mask including a vent system for ventilating the mask, a detector for providing respiration data of a user and located for sensing at least one physical property of air inside the breathing mask when worn by a user and a controller configured to activate the vent system based on the respiration data. The controller may be configured to predict future respiration data based on historic respiration data of at least one earlier detected inhaling or exhaling cycle, determine whether a future inhaling or exhaling cycle will occur based on predicted future respiration data and activate the vent system before the determined future inhaling or exhaling cycle commences.

20 Claims, 2 Drawing Sheets

(51) Int. Cl.
*A61M 16/00* (2006.01)
*A62B 18/02* (2006.01)
*A62B 18/10* (2006.01)
*A62B 23/02* (2006.01)
*A61M 16/16* (2006.01)
*A61M 16/10* (2006.01)

(52) U.S. Cl.
CPC .............. *A62B 18/08* (2013.01); *A62B 18/10* (2013.01); *A62B 23/02* (2013.01); *A61M 16/161* (2014.02); *A61M 2016/0027* (2013.01); *A61M 2016/103* (2013.01); *A61M 2016/1025* (2013.01); *A61M 2205/3334* (2013.01); *A61M 2205/3368* (2013.01)

(56) References Cited

U.S. PATENT DOCUMENTS

| | | | | |
|---|---|---|---|---|
| 2018/0078798 A1 * | 3/2018 | Fabian | .................. | A61B 5/6803 |
| 2018/0236275 A1 * | 8/2018 | Song | ...................... | A62B 23/02 |
| 2019/0358473 A1 * | 11/2019 | Szasz | .................. | G08B 21/182 |

FOREIGN PATENT DOCUMENTS

| | | | | |
|---|---|---|---|---|
| GB | 2523180 A * | 8/2015 | .......... | A61B 5/6803 |
| JP | 2008289600 A | 12/2008 | | |
| SG | 201309718 A1 | 7/2015 | | |
| WO | 2013039153 A1 | 3/2013 | | |
| WO | 2015084255 A1 | 6/2015 | | |
| WO | 2015183177 A1 | 12/2015 | | |
| WO | 2016157159 A1 | 10/2016 | | |

* cited by examiner

BREATHING MASK WITH INCREASED USER COMFORT

This application is the U.S. National Phase application under 35 U.S.C. § 371 of International Application No. PCT/EP2017/070851, filed on Aug. 17, 2017, which claims the benefit of International Application No. PCT/CN2016/096574, filed on Aug. 24, 2016 and International Application No. 16195216.3, filed Oct. 24, 2016. These applications are hereby incorporated by reference herein.

FIELD OF THE INVENTION

The present invention relates to breathing masks. In particular, the invention relates to breathing masks which increase the wearing comfort of the user.

BACKGROUND OF THE INVENTION

Breathing masks currently on the market are not comfortable to wear for a longer period of time because of the high breathing resistance. Also, the temperature, CO2 and humidity inside the mask increases when wearing the mask for a long period of time. This further decreases the wearing comfort.

Prior art devices solve the problem by installing active venting systems in the breathing mask. For example, WO/2015/183177 describes a breathing mask with an active venting system that is activated when the user is exhaling. However, such masks do not increase the user comfort as desired by the consumer.

A need exists for a breathing mask with improved user comfort over the existing products in combination with low power consumption.

SUMMARY OF THE INVENTION

In a first aspect of the invention, a breathing mask which can be worn by a user is presented. The mask comprises: a venting system for ventilating the mask; a detector for providing respiration data of a user wearing the mask and located such that at least one physical property of air inside the mask can be sensed, for example, at least one physical property of air inside the breathing mask when worn by a user; a controller configured to activate the venting system based on the respiration data. The controller is configured to: predict future respiration data based on historic respiration data of at least one earlier detected inhaling or exhaling cycle which was provided by the detector; determine whether a future inhaling or exhaling cycle will occur based on the predicted future respiration data; and activate the venting system before the determined future inhaling or exhaling cycle commences.

According to an embodiment, the controller is configured to predict a wave trend of the future respiration data based on the historic respiration data. Based on the predicted wave trend, the venting system is activated appropriately. According to an embodiment the controller is configured to predict the future respiration data based on slope values of respiration data. According to an embodiment, the wave trend is predicted based on slope values of respiration data. For example, the controller is configured to: determine a slope value of the real-time/current respiration data detected by the detector; and compare the slope value of the real-time/current respiration data with slope values of the historic respiration data.

According to an embodiment, the controller is configured to predict the future respiration data based on slope values of respiration data and a baseline value of the historic respiration data. According to an embodiment, the wave trend is predicted based on slope values of respiration data and a baseline value of the historic respiration data. For example, the controller is configured to: determine a baseline value of the historic respiration data; and compare the real-time/current respiration data detected by the detector with the determined baseline value to determine at which stage of the inhaling or exhaling cycle the current respiration data relates. Further, the controller is configured to determine a slope value of the real-time/current respiration data detected by the detector; and compare the slope value of the real-time/current respiration data with slope values of the historic respiration data.

According to an embodiment the controller is configured to adapt velocity of air flow produced by the venting system based on a pre-determined level of the at least one physical property. The pre-determined level may be set by the user via an input interface coupled to the controller. Alternatively, the controller may be configured to wirelessly receive data such as the pre-determined level, for example from a device, e.g. a smartphone, of a user via Wi-Fi, Bluetooth, ZigBee or other wireless technologies. The user may provide his preferences on, for example, temperature, humidity, carbon dioxide, pressure, oxygen levels, or a combination thereof.

According to an embodiment, the venting system is a unidirectional venting system adapted for drawing air out of the mask; and the controller is configured to activate the unidirectional venting system before the determined future exhaling cycle commences; and the controller is configured to stop the unidirectional venting system before the determined future inhaling cycle commences.

According to an embodiment the controller is configured to activate the venting system at least 75 milliseconds microseconds before the next inhaling or exhaling cycle starts. The controller may be configured to activate the venting system between 75 milliseconds and 150 milliseconds before the next inhaling or exhaling cycle starts.

According to an embodiment, the venting system comprises a first component adapted for drawing air out of the mask when worn by the user, and a second component adapted for drawing air into the mask when worn by a user; and the controller is configured to activate the first component before the determined future exhaling cycle commences; and the controller is configured to activate the second component before the determined future inhaling cycle commences.

According to an embodiment, the venting system is a bidirectional venting system comprising an air filter, and the controller is configured to activate the bidirectional venting system such that air is drawn out of the mask, for example when worn by a user, before the determined future exhaling cycle commences; and the controller is configured to activate the bidirectional venting system such that air is drawn into the mask, for example when worn by a user, before the determined future inhaling cycle commences.

According to an embodiment, the detector comprises a temperature sensor and/or a humidity sensor, the at least one physical parameter being temperature and/or humidity inside the mask when worn. According to an embodiment, the detector comprises a pressure sensor, and wherein the at least one physical property is pressure inside the mask when worn. According to an embodiment the detector comprises a carbon dioxide sensor, and the at least one physical property is carbon dioxide level inside the mask when worn.

According to an embodiment, the detector comprises an oxygen sensor, and the at least one physical property is oxygen level inside the mask when worn.

In a second aspect of the invention, a method for controlling a venting system of a breathing mask is presented. The method comprises: receiving historic respiration data of at least one inhaling or exhaling cycle, for example of a user wearing the mask; predicting future respiration data based on the historic respiration data; determining whether a future inhaling or exhaling cycle will occur based on the predicted future respiration data; and activating the venting system before the determined future inhaling or exhaling cycle commences.

According to an embodiment, predicting the future respiration data based on the historic respiration data comprises predicting a wave trend of future respiration data based on the historic respiration data. According to an embodiment predicting the future respiration data based on the historic respiration data comprises predicting the future respiration data based on slope values of current and historic respiration data.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Any reference signs in the claims shall not be construed as limiting the scope.

In the different drawings, the same reference signs refer to the same or analogous elements.

DETAILED DESCRIPTION OF THE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Throughout this disclosure, reference is made to "breathing mask" and "inside space". The breathing mask is a mask that is worn by a user and filters outside air before reaching the user's mouth or nose. The mask prevents particles such as pollutants from reaching the airways of the user. Typical breathing mask are worn in polluted environments such as congested cities. When the user wears the mask an inside space is created between the face of the user and the mask itself. This inside space is filled with filtered outside air when the user inhales and with air from the breath of the user when the user exhales.

In a first aspect of the invention, a breathing mask is presented. The breathing mask comprises a venting system for ventilating the mask. Such a ventilating system may comprise an active ventilating system such as a fan or a micro-fan. The active ventilating system may also be a valve, e.g. an electrically controlled valve.

Further, a detector is located in or on the mask. The detector is located such that at least one physical property of air inside the mask, in the inside space of the mask when worn by the user, can be sensed. At least one physical property of air present in the inside space can be sensed by the detector. The at least one physical property of air represents respiration data of the user wearing the mask. The at least one physical property of air may be temperature, pressure, humidity, CO2 level, O2 level or a combination of those. The detector may be any optically or electrically based component capable of sensing one or more physical properties of air.

Further, a controller is present in or on the mask. The controller may be a processor or a micro-controller. The controller is coupled wired or wirelessly to the detector such that the respiration data from the detector can be received by the controller. The controller is further coupled to the venting system and is configured to activate the venting system based on the received respiration data. The controller is further configured to predict future respiration data based on historic respiration data of at least one earlier detected inhaling or exhaling cycle. Thus, while the user is wearing the mask, the detector is providing the respiration data of the user. This respiration data is received by the controller and is stored in a memory internally or externally to the controller. The controller is further configured to: predict future respiration data based on the stored respiration data; determine whether a future inhaling or exhaling cycle will occur based on predicted future respiration data; and activate the venting system before the determined future inhaling or exhaling cycle commences.

The venting system is activated based on predicted future respiration data. By doing so, the venting system is activated before the actual inhaling or exhaling cycle begins. It is an advantage of the invention that instead of using a threshold value of a physical parameter of air inside the mask to control the venting system, the active venting system can be more accurately controlled using the predicted data which results in better ventilation and increased user comfort. The more accurate ventilation results in lower temperature, lower humidity level and lower carbon dioxide levels in the mask. It is a further advantage of the invention that through this accurate control of the venting system, power can be saved which is a critical parameter for battery powered portable breathing mask devices.

Figure 1:
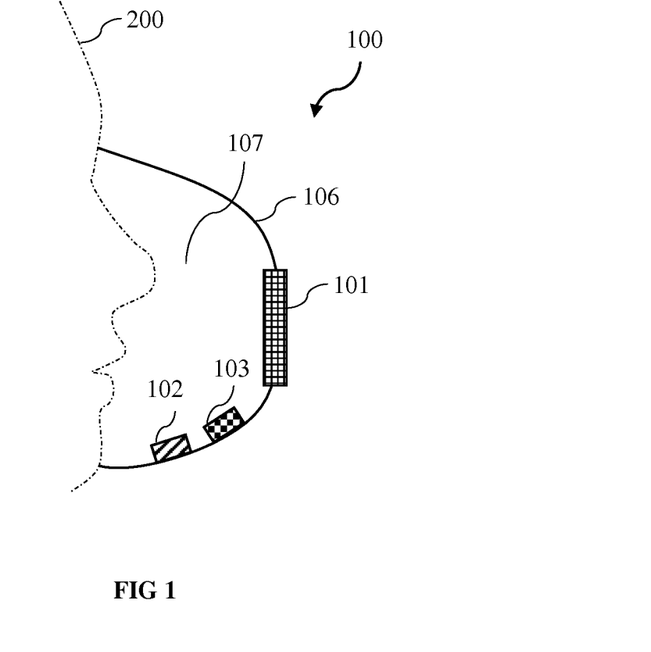
FIG. 1 illustrates an embodiment of a breathing mask worn by a user

FIG. 1 illustrates an embodiment of a breathing mask 100 worn by a user 200. When worn, an inside space 107 is present between the user 200 and the breathing mask 100. In the inside space 107 exchange of air takes place between air within the inside space 107 and air outside of the mask. In this embodiment the cover 106 of the breathing mask 100 covers the mouth and nose of the user 200. Cover 106 functions as the air filter of the breathing mask 100. Cover 106 is manufactured from a material that prevents pollutants in the outside air from reaching the mouth and nose of user 200 such that only clean air is provided to the user's mouth and nose. Venting system 101 is located in cover 106 such that air from inside the breathing mask can be exported from the mask. The cover 106 is shaped such that a snug fit with the user's face is achieved when worn. The detector 102 is located on or in the cover 106 facing the inside space 107 such that a physical parameter of air in the inside space 107 can be sensed. The controller 103 is located on or in the cover 106 and is coupled (not illustrated) to the detector and the venting system 101. A battery (not illustrated) may be present to power electronic components of the breathing mask 100. The battery may be located on the cover 106.

In embodiments of the invention, the breathing mask covers only the mouth or the nose of the user. In other embodiments, both are covered.

In embodiments of the invention, a battery is present for providing power to the detector, controller and venting system. In embodiments of the invention, a chargeable battery is presented coupled to a generator adapted for generating electricity from inhaling or exhaling cycles of the user.

According to an embodiment of the invention, the controller is configured to predict a wave trend of the future respiration data based on the historic respiration data. Upon assessment of the future respiration data, the active venting system is activated.

According to a particular embodiment, the prediction future respiration data is based on slope values of respiration data. According to a particular embodiment, the prediction future respiration data is based on slope values of current and historic respiration data. Thus, slope values are used as the future breath wave prediction value input. According to an embodiment, the controller is configured to: determine a slope value of real-time or current respiration data detected by the detector; and compare the slope value of the current respiration data with slope values of the historic respiration data.

According to an embodiment of the invention, the wave baseline value of the historic respiration data is determined. The baseline is calculated based on the average of the maximum and minimum sampled values of the historic respiration data.

$$\text{Baseline} = (T_{max} + T_{min})/2$$

T represents the temperature, but the baseline value can also be determined using maximum and minimum sampled values of pressure, humidity, CO2 or O2. The historical baseline value may be stored in the controller. The controller calculates the averaged baseline value from at least one breath cycle, e.g. four cycles. As a result, the controller is further configured to take into account this wave baseline value to accurately determine at which stage of the inhaling or exhaling cycle the current respiration data relates and to relate a determined slope value of current respiration data to that stage. Thus, the determination whether a future inhaling or exhaling cycle will occur based on predicted future respiration data is performed more accurately using the wave baseline information of the historic respiration data.

Example

Real-time data from the detector is being received by the controller. The controller calculates the instantaneous slope signal of the received real-time data. The real time data is compared with the determined baseline to determine at which stage of an inhaling or exhaling cycle the user is. For example, to determine whether the real-time data relates to the first half of an inhaling/exhaling cycle or a second half of an inhaling/exhaling cycle. This comparison is important as slope values of the real-time data may be equal for different stages of an inhaling or an exhaling cycle. The controller is configured to activate the venting system only when an inhaling cycle or an exhaling cycle is at the second half of the inhaling or exhaling cycle. The instantaneous slope signal is also compared with calculated slope signals from at least one previous inhaling and/or exhaling cycle or with averaged calculated slope values of more than one inhaling and/or exhaling cycle, e.g. four cycles. Thus, from the slope comparison and the baseline value comparison, it is accurately determined at which point in time the user will switch from an inhaling cycle to an exhaling cycle or at which point in time the user will switch from an exhaling cycle to an inhaling cycle. Before this switch happens, the controller instructs the venting system to activate appropriately depending on the type of the next cycle that will take place.

According to an embodiment of the invention, the historic respiration data represents data from at least one inhaling and/or exhaling cycle that took place. Preferably, the historic respiration data represents data from at least 4 inhaling and/or exhaling cycles that took place.

Figure 2:
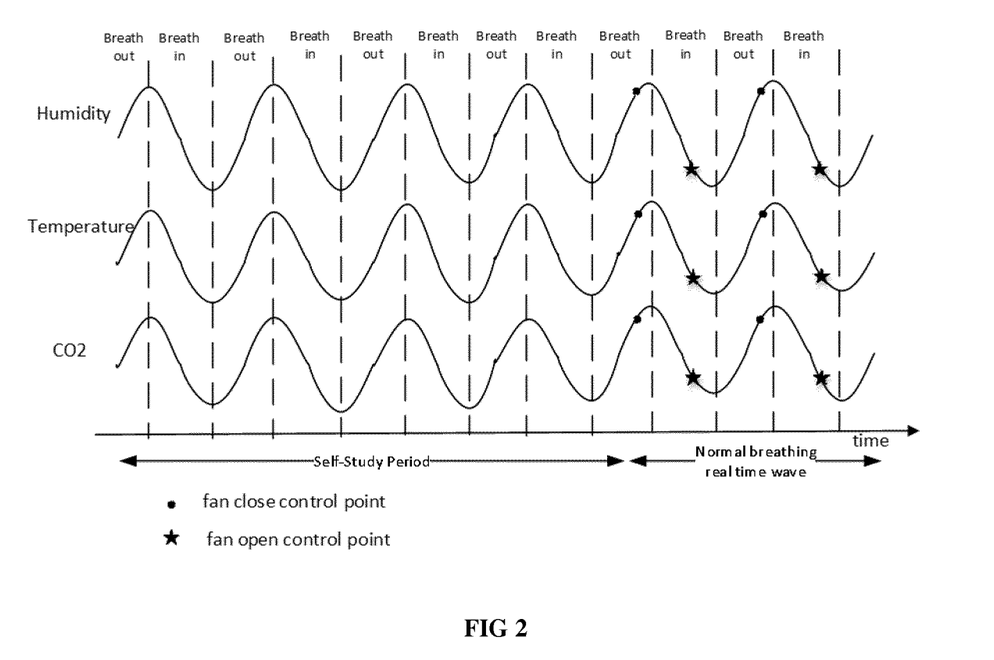
FIG. 2 illustrates the use of historic respiration data to determine the close and open control point of a fan

FIG. 2 illustrates how self-study period of the breathing mask which consisting of 4 breathing periods, each breathing period consists of an inhaling and an exhaling cycle. Based on the data acquired during the self-study period and based on the real-time data sensed by the detector it is determined when the next inhaling or exhaling cycle will start. Before the next cycle starts, the venting system of the mask is controlled appropriately.

According to an embodiment of the invention, the historic respiration data of the inhaling and/or exhaling cycles is averaged and used to predict future respiration data.

According to an embodiment of the invention, the controller is configured to continuously store respiration data of at least one inhaling and/or exhaling cycle, e.g. four cycles that took place. Thus, while the user is using the mask, the historic respiration data is continuously updated with respiration data of the one or more of the previous inhaling and/or exhaling cycles. In other words, the controller is configured to store historic respiration data using a data based sliding window.

According to an embodiment of the invention, the controller is configured to adapt the velocity of the air flow produced by the venting system based on a pre-determined level of the at least one physical property. For example, when the venting system is a fan, the controller is configured to increase or decrease the speed of the fan based on real-time physical property data or air sensed by the detector and a pre-determined level of the at least one physical property. The technical effect is that when a pre-determined value of certain physical property of air inside the mask is exceeded, e.g. temperature, humidity level, CO2 level, pressure, O2 level, the speed of the fan can be increased to reduce the level of the sensed physical property. Also, when a certain physical property of air inside the mask is below a pre-determined value, e.g., temperature, humidity level, CO2 level, pressure, O2 level, the speed of the fan can be decreased to increase the level of the sensed physical property. As an advantage, the user comfort is further increased. The pre-determined level of the at least one physical property may be set by the user. For example, the user may set the physical properties of air that are comfortable to him. This allows a customization of the mask by the user. For example, the user may choose different pre-determined levels in different seasons of the year or in different parts of the world, e.g. temperature, humidity.

According to an embodiment of the invention, the venting system is a unidirectional venting system adapted for drawing air out of the mask, for example when a user exhales. The controller is adapted to activate the unidirectional venting system before the determined future exhaling cycle commences. This ensures that the air in the inside space of the mask is expelled and does not create a discomfort to the user during usage. The controller may be further adapted to stop the unidirectional venting system before the determined future inhaling cycle commences. According to a particular embodiment of the invention, the unidirectional venting system is configured to prevent air from entering the mask via the unidirectional venting system when the unidirectional venting system is not active. For example, the unidirectional venting system may comprise a valve configured to close when the unidirectional venting system is not active. In the case of an active valve, the valve may be coupled to the controller and fed with the same control signal of the unidirectional venting system. Alternatively, the valve is a passive valve adapted to close when pressure inside the mask is below a pre-determined threshold.

According to an embodiment of the invention, the venting system comprises a first and a second venting component. A first venting component is adapted to draw air out of the mask, for example when worn by a user. The first venting component may be a fan or a micro-fan. A venting second component is adapted to draw air into the mask, for example when worn by a user. The second venting component may be a fan or a micro-fan. The controller is configured to activate the first venting component before the determined future exhaling cycle commences. The controller is further configured to activate the second venting component before the determined future inhaling cycle commences. Hence, the first and the second venting components are controlled separate from each other by the controller based on the predicted respiration data.

Figure 3:
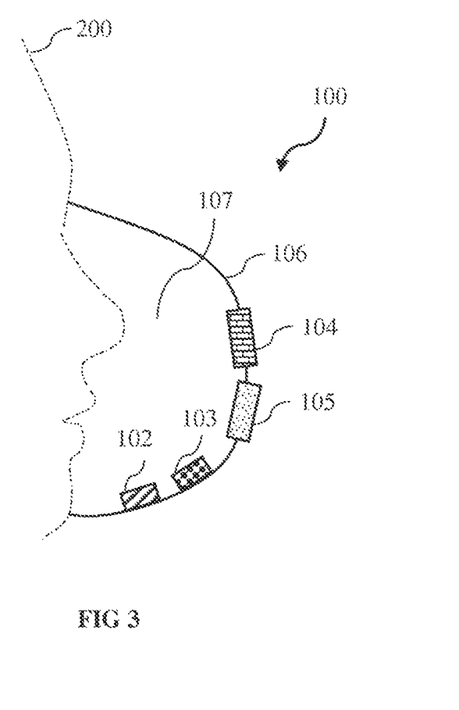
FIG. 3 illustrates an embodiment of a breathing mask worn by a user featuring two separate venting components

FIG. 3 illustrates an embodiment of the invention. Breathing mask 100 comprises a cover 106. In the cover 106 two venting components 104, 105 are present. Both venting components 104, 105 are coupled to the controller 103 which is also located on the cover 106. A first venting component 104 is activated by the controller and is adapted to draw out air from inside the breathing mask 100 to the outside, e.g. to the surrounding environment, from inside space 107 to the outside of the mask 100. A second venting component 105 is activated by the controller 103 and is adapted to draw in air from outside into the breathing mask 100 into inside space 107. Further, a detector 102 is present and located such that at least one physical parameter of air can be sensed in inside space 107.

According to a particular embodiment, the second venting component comprises an air filter such that air drawn into the mask is filtered before reaching the user. For example, the air filter is integrated in the second venting component.

Figure 4:
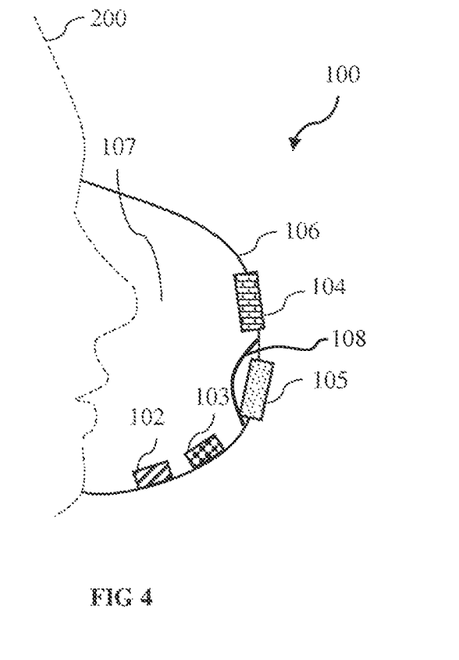
FIG. 4 illustrates an embodiment of a breathing mask worn by a user featuring two separate venting components, one of the venting components featuring an external air filter The drawings are only schematic and are non-limiting. In the drawings, the size of some of the elements may be exaggerated and not drawn on scale for illustrative purposes.

According to an embodiment of the invention, the breathing mask comprises an air filter located such that air drawn into the mask by the second venting component is filtered before reaching the user. For example, when the mask is worn by a user, the air filter is located in between the second venting component and the face of the user. FIG. 4 illustrates such an embodiment.

FIG. 4 illustrates an embodiment of a breathing mask 100. The breathing mask 100 is similar to the breathing mask depicted in FIG. 3. However, in addition to the features of the mask in FIG. 3, the mask comprises an air filter 108 which is located on the cover 106. The first venting component 104 is located in the cover 106. The air filter 108 is located such that air drawn from outside to the inside space 107 of the breathing mask 100 passes through the air filter 108, for example before reaching the user 200.

According to an embodiment of the invention, the first venting component may comprise a first valve. The first valve is adapted to close when the first venting component is inactive. For example, the first valve may be a passive valve adapted to open when air is drawn out of the mask and to close when air is drawn into the mask. The first valve may also be an active valve coupled to the controller. For example, the first valve is controlled by the same signal that is supplied to the first venting component. Thus, the controller is configured to open the first valve before the determined future exhaling cycle commences and to close the first valve before the determined future inhaling cycle commences.

According to an embodiment of the invention, the second venting component may comprise a second valve. The second valve is adapted to close when the second component is inactive. For example, the second valve may be a passive valve adapted to open when air is drawn into mask and to close when air is drawn out of the mask. The second valve may also be an active valve coupled to the controller. For example, the second valve is controlled by the same signal that is supplied to the second venting component. Thus, the controller is configured to open the second valve before the determined future inhaling cycle commences and to close the second valve before the determined future exhaling cycle commences.

According to an embodiment of the invention, the venting system comprises a bidirectional venting system adapted for drawing air into the mask and drawing air out of the mask. For example, the bidirectional venting system is a bidirectional fan capable of drawing air into the mask by rotating the fan in one direction and drawing out air of the mask by rotating the fan in the opposite direction. The controller is configured to activate the venting system such that air is drawn out of the mask before a determined future exhaling cycle commences. The controller is further configured to activate the venting system such that air is drawn into the mask before the determined future inhaling cycle commences.

According to a particular embodiment, the bidirectional venting system comprises an air filter such that air drawn into the mask is filtered before reaching the user. For example, the air filter is integrated in the bidirectional venting system.

According to an embodiment of the invention, the breathing mask comprises an air filter located such that air drawn into the mask by the bidirectional venting system is filtered before reaching the user. For example, when the mask is worn by a user, the air filter is located in between the bidirectional venting system and the user.

According to an embodiment of the invention, the detector comprises a temperature sensor located to sense temperature inside the mask when worn by the user. Thus, when the user wears the mask, the temperature in the inside space of the mask can be measured. In this embodiment, the at least one physical property is temperature. The sensor may be a Sensirion STS3x sensor.

According to an embodiment of the invention, the detector comprises a humidity sensor located to sense humidity of air inside the mask when worn by the user. Thus, when the user wears the mask, the humidity in the inside space of the mask can be measured. In this embodiment, the at least one physical property is relative humidity. The sensor may be a Sensirion SHT3x sensor. The sensor may be controlled by the micro-controller through SPI, I2C or UART interface. The sample rate may be controlled into a relative high mode, such as 10 Hz sample rate or a much higher sample rate.

According to an embodiment of the invention, the detector comprises a pressure sensor located to sense pressure inside the mask when worn by the user. Thus, when the user wears the mask, the pressure in the inside space of the mask can be measured. In this embodiment, the at least one physical property is pressure. The sensor may be a differential sensor from the Sensirion SPD60x series. The measurement range is −500 to 500 Pa. This covers the breath pressure range.

According to an embodiment of the invention, the detector comprises a carbon dioxide sensor located to sense a carbon dioxide level of air inside the mask when worn by the user. Thus, when the user wears the mask, the carbon dioxide level in the inside space of the mask can be measured. In this embodiment, the at least one physical property of air is carbon dioxide level. The sensor may be a GC-0017 carbon dioxide meter.

According to an embodiment of the invention, the detector comprises an oxygen sensor located to sense an oxygen level of air inside the mask when worn by the user. Thus, when the user wears the mask, the oxygen level in the inside space of the mask can be measured. In this embodiment, the at least one physical property of air is oxygen level.

According to an embodiment of the invention, the detector may comprise a combination of any of the sensors described above.

According to embodiments of the invention, respiration data may be measured, detected or recorded using a detector present in the breathing mask or the respiration data may be received from a device capable of detecting, recording or measuring respiration data, external from the breathing mask.

According to a second aspect of the invention, a method for controlling a venting system of a breathing mask is presented. In a first step, historic respiration data of at least one previous inhaling and exhaling cycles is received. This data is stored. In a second step, using the historic respiration data of the at least one previous inhaling and exhaling cycle future respiration data is predicted. In a third step it is determined based on the predicted future respiration data whether a future inhaling or exhaling cycle will occur. In a fourth step it is decided to activate the venting system accordingly in response to whether the future respiration cycle is an inhaling or an exhaling cycle.

According to an embodiment of the invention, predicting the future respiration data based on the historic respiration data comprises predicting a wave trend of future respiration data based on the historic respiration data.

According to an embodiment of the invention, predicting the future respiration data based on the historic respiration data comprises predicting the future respiration data based on slope values of current and historic respiration data.

According to an embodiment of the invention, predicting the future respiration data based on the historic respiration data comprises determining a slope value of real-time respiration data; and comparing the real-time slope value slope values of a historic respiration data.

The invention claimed is:
1. A breathing mask, comprising:
a vent system for ventilating the mask;
a detector for providing respiration data of a user wearing the mask, and wherein the detector is located such that at least one physical property of air inside the breathing mask can be detected;
a controller configured to activate the vent system based on the respiration data;

wherein
the controller is configured to:
  predict future respiration data based on historic respiration data of at least one earlier detected inhaling or exhaling cycle; and
  determine whether a future inhaling or exhaling cycle will occur based on the predicted future respiration data;
  activate the vent system before the determined future inhaling or exhaling cycle commences,
wherein the controller is configured to predict the future respiration data based on slope values of respiration data and a baseline value of the historic respiration data.

2. The breathing mask according to claim 1, wherein the controller is configured to predict a wave trend of future respiration data based on the historic respiration data.

3. The breathing mask according to claim 1, wherein the predicting the future respiration data comprises:
  determining the baseline value of the historic respiration data;
  comparing current respiration data with the determined baseline value to determine to which stage of the inhaling or exhaling cycle the current respiration data relates;
  determining a slope value of the current respiration data detected by the detector; and
  comparing the slope value of the current respiration data with slope values of the historic respiration data.

4. The breathing mask according to claim 1, wherein the controller is configured to adapt velocity of air flow produced by the vent system based on a pre-determined level of the at least one physical property.

5. The breathing mask according to claim 1,
  wherein the vent system is a unidirectional vent system adapted for drawing air out of the mask; and
  wherein the controller is configured to activate the unidirectional vent system before the determined future exhaling cycle commences; and
  wherein the controller is configured to stop the unidirectional vent system before the determined future inhaling cycle commences.

6. The breathing mask according to claim 1,
  wherein the vent system comprises a first component adapted for drawing air out of the mask, and a second component adapted for drawing air into the mask; and
  wherein the controller is configured to activate the first component before the determined future exhaling cycle commences; and
  wherein the controller is configured to activate the second component before the determined future inhaling cycle commences.

7. The breathing mask according to claim 1, wherein the vent system is a bidirectional vent system comprising an air filter, and
  wherein the controller is configured to activate the vent system such that air is drawn out of the mask before the determined future exhaling cycle commences; and
  wherein the controller is configured to activate the vent system such that air is drawn into the mask before the determined future inhaling cycle commences.

8. The breathing mask according to claim 1, wherein the detector comprises a temperature sensor and/or a humidity sensor.

9. The breathing mask according to claim 1, wherein the detector comprises a pressure sensor, and wherein the at least one physical property is pressure.

10. The breathing mask according to claim 1, wherein the detector comprises a carbon dioxide sensor, and wherein the at least one physical property is carbon dioxide level.

11. The breathing mask according to claim 1, wherein the detector comprises an oxygen sensor, wherein the at least one physical property is oxygen level.

12. A method for controlling a vent system of a breathing mask, the method comprising acts of:
  receiving historic respiration data of at east one inhaling or exhaling cycle of a user wearing the mask;
  predicting future respiration data based on the historic respiration data;
  determining whether a future inhaling or exhaling cycle will occur based on the predicted future respiration data;
  activating the vent system before the determined future inhaling or exhaling cycle commences,
  wherein predicting the future respiration data comprises an act of predicting the future respiration data based on slope values of respiration data and a baseline value of the historic respiration data.

13. The method according to claim 12, wherein predicting the future respiration data based on the historic respiration data comprises predicting a wave trend of future respiration data based on the historic respiration data.

14. The method according to claim 12, wherein predicting the future respiration data based on the historic respiration data comprises acts of:
  determining the baseline value of the historic respiration data;
  comparing current respiration data with the determined baseline value to determine to which stage of the inhaling or exhaling cycle the current respiration data relates;
  determining a slope value of the current respiration data detected by the detector; and
  comparing the slope value of the current respiration data with slope values of the historic respiration data.

15. A breathing mask, comprising:
  a vent configured to ventilate the mask;
  a detector configured to provide respiration data of a user wearing the mask based on at least one physical property of air inside the mask;
  a controller configured to activate the vent based on the respiration data;
  wherein the controller is configured to:
    predict future respiration data based on slope values of respiration data and a baseline value of historic respiration data of at least one earlier detected inhaling or exhaling cycle; and
    determine whether a future inhaling or exhaling cycle will occur based on the predicted future respiration data;
    activate the vent before the determined future inhaling or exhaling cycle commences.

16. The mask according to claim 15, the controller is configured to:
  determine the baseline value of the historic respiration data;
  compare current respiration data with the determined baseline value to determine to which stage of the inhaling or exhaling cycle the current respiration data relates;
  determine a slope value of the current respiration data detected by the detector; and
  compare the slope value of the current respiration data with slope values of the historic respiration data.

17. The mask according to claim 15, comprising a fan or micro-fan configured to operate together with the vent to ventilate the mask.

18. A method for controlling a vent of a breathing mask, the method comprising acts of:
   receiving historic respiration data of at least one inhaling or exhaling cycle of a user wearing the mask;
   predicting future respiration data based on slope values of respiration data and a baseline value of the historic respiration data;
   determining whether a future inhaling or exhaling cycle will occur based on the predicted future respiration data;
   activating the vent before the determined future inhaling or exhaling cycle commences.

19. The method according to claim 18, comprising acts of:
   determining the baseline value of the historic respiration data;
   comparing current respiration data with the determined baseline value to determine to which stage of the inhaling or exhaling cycle the current respiration data relates;
   determining a slope value of the current respiration data detected by the detector; and
   comparing the slope value of the current respiration data with slope values of the historic respiration data.

20. The method according to claim 18, comprising an act of operating a fan or micro-fan together with the vent to ventilate the mask.

* * * * *